United States Patent [19]

Ruenitz

[11] Patent Number: 5,189,212
[45] Date of Patent: Feb. 23, 1993

[54] TRIARYLETHYLENE CARBOXYLIC ACIDS WITH ESTROGENIC ACTIVITY

[75] Inventor: Peter C. Ruenitz, Clarke City, Ga.

[73] Assignee: University of Georgia Research Foundation, Inc., Athens, Ga.

[21] Appl. No.: 579,398

[22] Filed: Sep. 7, 1990

[51] Int. Cl.$^5$ .............. C07C 59/40; C07C 69/76; A01N 37/10
[52] U.S. Cl. .................. 562/468; 562/491; 562/584; 560/57; 560/101
[58] Field of Search ............. 562/468, 491; 514/532, 514/569, 570; 560/57, 101; 569/584

[56] References Cited

U.S. PATENT DOCUMENTS

| | | | |
|---|---|---|---|
| 2,914,563 | 11/1959 | Allen | 562/584 |
| 4,729,999 | 3/1988 | Young | 514/569 |
| 4,851,433 | 7/1989 | Kraus . | |

OTHER PUBLICATIONS

Jarman et al., *Journal of Chem. Res. Synop.* (4), pp. 116–117, 1985.
Johnson, David W., "Synthesis of Haptens Related to (Z)- and (E)-Clomiphene", *Aust. J. Chem.*, vol. 33, pp. 461–464 (1980).
Jarmen et al., *J. Chem. Research* (M), 1985, 1342–1388 supporting microfiche for J. Chem. Research(S), 1985, 116–117.
McCague, R., *J. Chem. Research* (S), 58 (1986).
Ruenitz, P. C., et al., *J. Med. Chem.*, 25, 1056–1060 (1982).
Coe, P. L. et al., *J. Chem. Soc. Perkin Trans. I*, 475 (1986).
Johnson, M. D., et al., *Anti-Ostrogens and MCF-7 Cells*, The MacMillan Press Ltd., 1989.
Stevenson, D., et al., *J. Pharm. & Biomed. Analysis*, 6, 1065–1068, (1988).
Armstrong, R. D., et al., *Journal of Chromatography*, 414, 192–196 (1987).
Adam, H. K., et al., *Biochem. Pharmacology*, 27, 145–147, (1979).
Ruenitz, P. C., et al., *Drug Metabolism and Disposition*, 13, 5, (1985).
Katzenellenbogen, J., et al., *Journal of Labelled Compounds and Radiopharmaceuticals*, vol. XVIII, No. 6 (1980).

(List continued on next page.)

Primary Examiner—Jose G. Dees
Assistant Examiner—Keith MacMillan
Attorney, Agent, or Firm—Kilpatrick & Cody

[57] ABSTRACT

Nonsteroidal estrogenic triarylethylene carboxylic acids of the formula

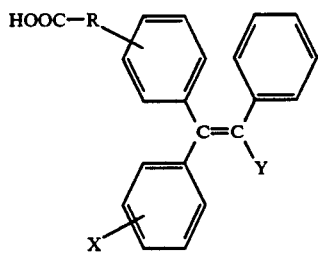

wherein R is $(CH_2)_mO$ or $(CH_2)_n$, where m is an integer from 1 to 4 and n is an integer from 0 to 4, X is hydrogen or hydroxyl, Y is methyl, ethyl, chlorine, or bromine, and wherein the RCOOH and X moieties are either meta or para to the phenyl ethylene linkage. Examples of active compounds include 4-hydroxytamoxifen acid, 3-hydroxytamoxifen acid, 4-[1-(p-hydroxyphenyl)-2-phenyl-1-butenyl]benzoic acid and 4-[1-(p-hydroxyphenyl)-2-phenyl-1-butenyl]phenylacetic acid. Compositions containing these triarylethylene carboxylic acids can be administered to patients to alleviate medical conditions associated with a deficiency of estrogen, including osteoporosis, premenstrual syndrome, vasomotor symptoms associated with menopause, atrophic vaginitis, Kraurosis vulvae, female hypogonadism, primary ovarian failure, excessive hair growth and prostatic cancer.

29 Claims, 3 Drawing Sheets

OTHER PUBLICATIONS

McCague, R., et al., *J. Med. Chem.*, 31, 1285-1290 (1988).

McCague, R., et al., *J. Med. Chem.*, 32, 2527-2533 (1989).

Foster, A. B., et al., *J. Med. Chem.*, 28, 1491-1497 (1985).

Reidy, G. F., et al., *Biochemical Pharmacology*, 38 (1), 195-199 (1989).

Kikuta, C., et al., *J. Pharmaceutical & Biomedical Analysis*, 7, 329-337 (1989).

Bain, R., et al., *Biochem. Pharmacology*, 32(2), 373 (1983).

Soininen, K., et al., *J. Int. Med. Res.* 14, 162 (1986).

Parr, I. B., et al., *Biochemical Pharmacology*, 36(9), 1513-1519 (1987).

Lien, E. A., et al., *Cancer Research*, 48, 2304-2308 (1988).

Kemp, J. V., et al., *Biochemical Pharmacology*, 32 (13), 2045-2052 (1983).

Fromson, J. M., et al., *Xenobiotica*, 3 (11), 711-714 (1973).

Fromson, J. M., et al., *Xenobiotica*, 3 (11) 693-709 (1973).

Jordan, V. C., et al., *Cancer Research*, 43, 1446-1450 (1983).

Simberg, N. H., et al., *J. Steroid Biochem.*, 36 (3), 197-202 (1990).

Sipila, H., et al., *J. Steroid Biochem.*, 36 (3) 211-215 (1990).

Hasan, S. A., et al., *Analytical Letters*, 23(2), 327-334 (1990).

| COMPOUND | R | X |
|---|---|---|
| TAMOXIFEN ACID | $OCH_2CO_2H$ | H |
| 4-HYDROXY TAMOXIFEN ACID | $OCH_2CO_2H$ | OH |
| TAMOXIFEN | $OCH_2CH_2N(CH_3)_2$ | H |
| 4-HYDROXYTAMOXIFEN | $OCH_2CH_2N(CH_3)_2$ | OH |

TRIARYLETHYLENE CARBOXYLIC ACIDS WITH ESTROGENIC ACTIVITY

The U.S. Government has certain rights in this invention by virtue of grants from the National Institutes of Health.

This invention relates to triarylethylene carboxylic acids with estrogenic activity and their method of use.

BACKGROUND OF THE INVENTION

Steroidal hormones are organic molecules that are synthesized in the body in an organ or gland and then carried through the blood to induce activity at a remote location. Steroidal hormones contain a perhydrocyclopentanophenanthrene moiety. Estrogens are an important class of steroidal hormones that stimulate the development and maintenance of fundamental sexual characteristics in humans. The principal naturally occurring estrogen in humans is estradiol, that plays a pivotal role in the regulation and maintenance of the androgen/estrogen balance. Estrogens have also been found useful in the treatment of certain medical conditions and diseases. For example, estradiol, a steroid hormone produced by the ovary, is useful in the treatment of osteoporosis, premenstrual syndrome, vasomotor symptoms associated with menopause, atrophic vaginitis, Kraurosis vulvae, female hypogonadism, primary ovarian failure, excessive hair growth and prostatic cancer. Estrogens are also used in combination with another female sex hormone, progesterone, to promote gonadotropin suppression and to act as an oral contraceptive.

Diethylstilbestrol, conjugated estrogens, and ethinyl estradiol have been used as steroidal estrogen substitutes for pharmaceutical administration. However, administration of steroidal hormone substitutes have been associated with a number of side effects, including myocardial infarction, thromboembolism, cerebrovascular disease, and endometrial carcinoma. In fact, while estrogens and estrogen substitutes are currently the only known effective treatment for osteoporosis, their use is severely limited due to side effects of long term steroidal treatment. Further, no new estrogen substitutes have been marketed in the last twenty years, perhaps due to certain severe side effects, including devastating birth defects, that were found associated with administration of diethylstilbestrol.

In light of problems associated with steroidal therapy, a significant amount of research has been carried out to identify effective nonsteroidal estrogen and antiestrogenic compounds. An example of a nonsteroidal antiestrogen is tamoxifen (TAM), ((Z)-2-[4-(1,2-diphenyl-1-butenyl)phenoxy]-N,N-dimethylethanamine), which is a triphenylethylene derivative. The chemical structure of tamoxifen is illustrated in FIG. 1. Tamoxifen effectively antagonizes the growth-promoting effect of estrogens in primary target tissues such as the breast and ovum. Tamoxifen is currently marketed for treatment of breast cancer. Sales of this compound reached $200,000,000 in 1989.

In humans and in various animal species, TAM has been shown to undergo oxidative biotransformation to a number of basic or neutral oxidized metabolites. In particular, side chain alteration (N-demethylation, N,N-didemethylation and substitution of a hydroxyl group for the dimethylamino group), alone or in combination with 4-hydroxylation, has been shown to occur. 4-Hydroxy tamoxifen (4-HT) is a major metabolite. Acid metabolites of TAM, however, have not been detected.

Studies based on receptor competitive binding have shown that the basic and neutral metabolites of TAM generally possess estrogen receptor affinities and antiestrogenic activities that equal or exceed those of TAM itself. In addition, studies have demonstrated that these metabolites localize with TAM in tumors of patients on TAM therapy.

Clomiphene (2-[4-(2-chloro-1,2-diphenylethenyl)-phenoxy]-N,N-diethylethanamine) is a pharmaceutical compound closely structurally related to tamoxifen. The preparation of clomiphene is described in U.S. Pat. No. 2,914,563. Clomiphene is a nonsteroidal antiestrogen that is prescribed to induce ovulation in infertile women with physiological indications of normal estrogen levels. In the hypothalamus, clomiphene antagonizes estradiol-mediated feedback inhibition of gonadotrophin-releasing hormone secretion. Tamoxifen has also been administered to initiate ovulation in anovulatory women, and is favored therapeutically over clomiphene for this purpose because it has a lower incidence of side effects.

U.S. Pat. No. 4,894,373 to Young describes the use of clomiphene, tamoxifen, nafoxidene, and other antiestrogenic compounds in the treatment of menopause and osteoporosis.

Toremifene (2-[4-(2-chloromethyl-1,2-diphenylethenyl)phenoxy]-N,N-diethylethanamine), is a triphenylethylene compound structurally related to tamoxifen that has antineoplastic activity Hasan, *Analyt. Letters* 23(2), 327–334 (1990), reported that toremifene is metabolized in vivo to a number of compounds, including two metabolites in which the diethylethanamine side chain is replaced with oxyacetic acid and the methyl ester of oxyacetic acid. No biological activities have been reported for these metabolites.

While several nonsteroidal antiestrogenic compounds have been developed, very few nonsteroidal estrogenic compounds have been identified. There is strong need for nonsteroidal estrogenic compounds for use in estrogen replacement therapy, and specifically menopause therapy. It has been estimated that one-fourth of all women seek medical advice or treatment for this condition. Nonsteroidal estrogenic compounds are also needed for osteoporosis therapy, in the prevention of uterine bleeding, failure of ovarian development at the age of puberty, prevention of excessive growth of body hair, and for oral contraceptives.

Therefore, it is an object of the present invention to provide nonsteroidal compounds with estrogenic activity.

SUMMARY OF THE INVENTION

Triarylethylene carboxylic acids of formula (I)

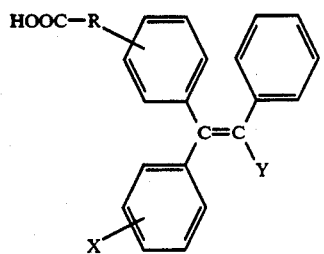

wherein R is $(CH_2)_mO$ or $(CH_2)_n$, where m is an integer from 1 to 4 and n is an integer from 0 to 4, X is hydrogen or hydroxyl, Y is methyl, ethyl, chlorine, or bromine, and wherein the RCOOH and X moieties are either meta or para to the phenyl ethylene linkage, have estrogenic activity. A preferred compound is 4-hydroxytamoxifen acid, (4-HTA; (E,Z)-2-{4-[1-(p-hydroxyphenyl)-2-phenyl]-1-butenyl}phenoxyacetic acid). In a preferred embodiment, X is hydroxyl. Examples of other TAM acid analogues, possessing significant structural and functional similarities to TA and 4-HTA, include, but are not limited to, 3-HTA, 4-[1-(p-hydroxyphenyl)-2-phenyl-1-butenyl]benzoic acid and 4-[1-(p-hydroxyphenyl)-2-phenyl-1-butenyl]phenylacetic acid.

Compounds of formula I other than wherein when X is hydrogen, R is $CH_2O$, and Y is ethyl (tamoxifen acid) have not previously been reported. Although tamoxifen acid has been synthesized, no biological activity has been reported for the compound.

It was quite unexpected to discover that this class of compounds has estrogenic activity, in light of the fact that it is well known that very close analogs such as tamoxifen and clomiphene have an opposite, antiestrogenic effect in vivo.

Tamoxifen acid (R=$CH_2O$, X=hydrogen, and Y=$CH_2CH_3$), 4-HTA (R=$CH_2O$, X=p-hydroxyl, and Y=$CH_2CH_3$), and tamoxifen have estrogen receptor affinities of 0.01, 21, and 1.8, respectively, relative to estradiol (affinity=100). Neither tamoxifen acid nor 4-HTA inhibits the growth of MCF 7 human breast cancer cells (as an antiestrogenic compound would), but both compounds reverse the growth inhibitory effect of the antiestrogenic compound TAM. The nonsteroidal estrogenic triarylethylene carboxylic acids are administered to patients as the free acid or a pharmaceutically acceptable salt in combination with pharmaceutical carriers suitable for topical, subcutaneous, intravenous or oral administration to alleviate conditions associated with a low level of estrogen, including osteoporosis, premenstrual syndrome, vasomotor symptoms associated with menopause, atrophic vaginitis, Kraurosis vulvae, female hypogonadism, primary ovarian failure, excessive hair growth and prostatic cancer.

The triarylethylene carboxylic acids are advantageous for pharmaceutical treatment of estrogen deficiencies because they are eliminated slowly from the body, and have high estrogen receptor affinity. Further, they are only minimally taken up into the uterus and ovary. Another advantage of the compounds is that they can be used for nonsteroidal estrogen replacement, avoiding the unfortunate side effects that accompany long term steroidal therapy.

DETAILED DESCRIPTION OF THE INVENTION

Figure 1:
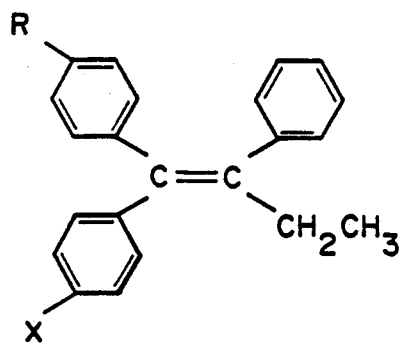
FIG. 1 is an illustration of the chemical structures of tamoxifen acid, 4-hydroxytamoxifen acid (4-HTA), tamoxifen (TAM), and 4-hydroxy tamoxifen (4-HT).

The following abbreviations are used throughout the specification: TAM, tamoxifen, (Z)-2-[4-(1,2-diphenyl-1-butenyl)phenoxy]-N,N-dimethylethanamine (FIG. 1)); 4-HT, 4-hydroxytamoxifen; TAM bis-phenol, 1,1-bis-(4-hydroxyphenyl)-2-phenyl-1-butene; TA, tamoxifen acid, (E,Z)-4-(1,2-diphenyl-1-butenyl)phenoxyacetic acid; TA-glyOH, (Z)-N-4-(1,2-diphenyl-1-butenyl)phenoxyacetylglycine; 4-HTA, 4-hydroxytamoxifen acid, (E,Z)-2-{4-[1-(p-hydroxyphenyl)-2-phenyl]-1-butenyl}phenoxyacetic acid; EIMS, electron ionization mass spectrometry; NMR, nuclear magnetic resonance spectrometry; TLC, thin layer chromatography; $R_f$, retardation factor.

I. SYNTHESIS OF COMPOUNDS OF FORMULA I

Tamoxifen acid is a known compound that can be synthesized according to the method of Jarman, et al., "The Use of Octafluorotoluene and Pentafluoropyridine in the Synthesis of pure Z- and E- Isomers of Derivatives of Tamoxifen (1,2-diphenyl-1-[4-(2-dimethylaminoethoxy)phenyl]but-1-ene}." *J. Chem. Research (M)*, 1339-1385 (1985).

Other triarylethylene carboxylic acids can be prepared using the McMurry reaction (Coe, et al., *J. Chem. Soc.* Perkin I 1986), the method described in European Patent Application 0126420 filed by Bristol Myers Corporation, or the reaction scheme described by Katzzenellenbogen, et al., *J. of Labeled Compounds and Radiopharmaceuticals*, Vol. XVIII(6) 885 (1981). The McMurry reaction involves the low valent titanium-mediated crossed coupling of a substituted benzophenone and the appropriate phenyl alkyl ketone. An example of the preparation of 4-hydroxy tamoxifen acid using the McMurry reaction is provided in Example 1. Triarylethylene carboxylic acids in which Y is a halogen can be prepared from the appropriate benzophenone and benzaldehyde followed by treatment of the product with N-chloro or N-bromo succinimide in dry chloroform for 4-5 hours.

Triarylethylene carboxylic acids can exist in the Z or E configuration. In the Z configuration (Z from the German zusammen, meaning together), the "higher priority" groups (according to the IUPAC and Cahn-Ingold-Prelog sequence rules) are cis. In the E configuration (E for entgegen, or opposite), the higher priorty groups are trans. It is known that there is facile isomerization of these isomers in solution. It is also known that isomerization can take place in acid, in which an alkenyl carbon can be protonated and twist about the former olefinic bond. For convenience, Formula I illustrates the triarylethylene carboxylic acids in the Z configuration. However, it should be understood that this invention includes both the Z and the E isomers of the compounds of Formula I. It should further be understood that the syntheses of the compounds of Formula I may be stereoselective, but they are not stereospecific. Therefore, both isomers will be obtained in the reaction schemes.

EXAMPLE 1

Synthesis of 4-HTA (E,Z)-2-(4-[1-(p-hydroxyphenyl)-2-phenyl]-1-butenyl) phenoxyacetic acid (4-HTA) was synthesized according to the following method.

General Procedures. Melting points (mp) were obtained on a capillary melting point apparatus and are uncorrected. Elemental analyses of all compounds prepared were within ±0.4% of calculated theoretical values. Reaction progress and purity of products were checked by analytical TLC using 0.2 mm silica gel plastic backed layers, and viewed under light of 254 nm wavelength. Proton NMR spectra were obtained at 90 mHz and EIMS were obtained using a direct ion probe. 4-(2-Bromoethoxy)-4'-hydroxybenzophenone was prepared by acylation of 2-phenoxyethyl bromide with 4-hydroxybenzoic acid: mp 136°-138° C.

Reaction of 4-(2-bromoethoxy)-4'-hydroxybenzophenone with propiophenone. To a stirred suspension of 2.3 grams (36 mg-atoms) of zinc in 25 mL of dry tetrahydrofuran, cooled to −10° C. and maintained under dry nitrogen, was added 3.4 grams (118 mmols) of titanium tetrachloride over a period of 0.25 hours. The mixture was then heated at reflux for 2 hours and returned to room temperature. A solution of 1.93 grams (6 mmols) of 4-(2-bromoethoxy)-4'-hydroxybenzophenone and 0.81 grams (6 mmols) of propiophenone in 25 mL of dry tetrahydrofuran was added dropwise. The mixture was stirred and refluxed for 4 hours. The cooled mixture was poured into 30 mL of 10% potassium carbonate in water. The mixture was extracted with two 50 mL portions of ether. The combined ether extracts were dried (sodium sulfate) and concentrated in vacuo to give 3.38 grams of crude product. This was dissolved in 10 mL of chloroform-benzene (1:1) and eluted through 15 grams of 60-200 mesh silica gel with a total of five column volumes (250 mL) of the above solvent after discarding the void volume. Concentration of the eluate afforded a yellow oil which was extracted with 40 mL of boiling hexanes. Storage at 8° C. gave 0.94 grams (38%) of light yellow crystals. Recrystallization from hexane afforded pure (E,Z)-2-(4-[1-(4-hydroxyphenyl)-2-phenyl]-1-butenyl}phenoxyethyl bromide as white needles, mp 123°-127° C.; $^1$H NMR (acetone-$d_6$) d 0.89 (t, 3H, CH$_3$), 2.47 (q, 2H, CH$_2$CH$_3$), 2.82 (s, 1H, OH), 3.66 and 3.77 (t, 2H total, CH$_2$Br), 4.21 and 4.38 (t, 2H total, CH$_2$OAr), 6.42-7.23 (m, 13H, arom.). The ratio of intensities of peaks at 4.21 ppm/4.38 ppm =0.25; 3.66 ppm/3.77 ppm=0.23. On this basis, the product is a mixture of 24% of the Z-isomer and 76% of th E-isomer.

Conversion to 4-Hydroxy Tamoxifen Acid. A mixture of 0.11 g (0.26 mmol) of (E,Z)-2-{4-[1-(4-hydroxyphenyl)-2-phenyl]-1-butenyl}phenoxyethyl bromide, 0.13 grams (0.78 mmol) of ethyl bromoacetate and 0.11 grams (0.78 mmol) of potassium carbonate in 1.5 mL of acetone was stirred and refluxed under a desiccant for 3 hours. Solvent was then evaporated in vacuo. The residue was dissolved in 1 mL of dioxane and 0.5 mL of 5% NaOH was added. After 15 minutes, the reaction mixture was evaporated. The solid product was shaken with 5 mL each of ether and 1% aqueous HCl. The aqueous phase was extracted two more times with 5 mL of ether. The combined ether extracts were dried and concentrated in vacuo to give 81 mg (64%) of a viscous oil which was dissolved in 5 mL of dimethyl formamide (DMF) containing 200 mg of NaCN. The mixture was stirred at room temperature for 45 hours. DMF was then evaporated in vacuo and the residue shaken with 5 mL of ether and 2 mL of 5% aqueous sodium bicarbonate. The aqueous phase was washed with another 3 mL of ether, and acidified with 10% aqueous sulfuric acid. The mixture was extracted twice with 3 mL of methylene chloride. The organic extracts were dried and concentrated in vacuo to give 68 mg of a viscous oil that was dissolved in about 1 mL of alcohol free chloroform. Storage at 8° C. overnight gave 27 mg (42%) of crystalline 4-HTA, which was dried overnight at 60° C./0.05 mm Hg: mp 215°-217° C. (decomposition); $^1$H NMR (chloroform-d) d 0.90 (t, J=7 Hz, 3H, CH$_3$), 2.45 (q, J=7 Hz, 2H, CCH$_2$), 4.50 and 4.66 (s, 0.8 and 1.2 H respectively, OCH$_2$), 6.50-7.25 (m, 13H, ArH); EIMS (70 eV) m/z (relative intensity) 374 (100, M+), 359 (20, M—CH$_3$), 315 (7, M—CH$_2$COOH).

II. Estrogenic Activity of Compounds of Formula I

The nonsteroidal triarylethylene carboxylic acids of Formula I possess estrogenic activity. 4-Hydroxy tamoxifen acid, one of the compounds in Formula I, has been found to be a potent estrogenic substitute. This activity is surprising in view of the known antiestrogenic activity of close analogs tamoxifen and its basic and neutral metabolites, as well as clomiphene.

The triarylethylene carboxylic acids resisted metabolic inactivation in the immature female rat and were not subject to accumulation in reproductive tissue In vitro studies demonstrate that these compounds interact with the estrogen receptor, with 4-HTA interacting to an extent and with activity comparable to estradiol.

The compounds of Formula I can be used to alleviate symptoms of diseases and medical conditions treatable with estrogen. Examples of such conditions include, but are not limited to, osteoporosis, premenstrual syndrome, vasomotor symptoms associated with menopause, atrophic vaginitis, Kraurosis vulvae, female hypogonadism, primary ovarian failure, excessive hair growth and prostatic carcinoma. In addition, these estrogenic compounds may be useful in combination with other hormones as contraceptives. A benefit of the claimed compounds is the relatively long retention time in the body, permitting less frequent administration of active compound and reducing the cost and discomfort of treatment to the patient.

EXAMPLE 2

Determination of Estrogen Receptor Affinity of Compounds of Formula I

The estrogen receptor affinity of the triarylethylenes of Formula I can be measured according to the method of Ruenitz, et.al., *J. Med. Chem.*, 25:1056, (1982).

[$^3$H]Estradiol (58 Ci/mmol) can be obtained from Amersham Corp., and its radiochemical purity checked by TLC. Uteri from Sprague-Dawley rats (200–250g) are homogenized (1 uterus/2 mL) in ice-cold 10 mM Tris buffer, pH 7.4, that contains 1.5 mM EDTA and 3 mM sodium azide (TEA buffer). The homogenate is centrifuged at 100000g for 1 hour at 4° C. Incubation mixtures should contain 200-μμL aliquots of the supernatant, and 10 μL of a solution of $1.1 \times 10^{-7}$M [$^3$H]estradiol in dimethylacetamide, and 10 μL unlabeled competitor in dimethylacetamide. Ten concentrations of competitor are used ranging from $1 \times 10^{-9}$ to $5 \times 10^{-5}$M. Control incubations should contain 10 μL of solvent alone. Nonspeoifio binding is determined in similarly prepared incubations that contain $1 \times 10^{-5}$M estradiol. Incubations should be performed in triplicate, in 5-mL polypropylene centrifuge tubes, at 2°–4° C. for 4 hours. Then a suspension of 400 μL of dextran-coated charcoal [0.1% dextran (Sigma no. D-1390), 1% acid-washed Norit A in TEA buffer]is added, and the incubation continues for 15 minutes at 2°–4° C. Tubes are then centrifuged at 1000g for 10 minutes, and 400-μL aliquots are dissolved in 5 mL of Scintivense (Fisher), Bound [$^3$H]estradiol is determined by liquid scintillation spectrometry. Quench corrections are made by the external standard method.

EXAMPLE 3

Determination of Estrogen Receptor Affinity of 4-Hydroxy Tamoxifen Acid

Figure 2:
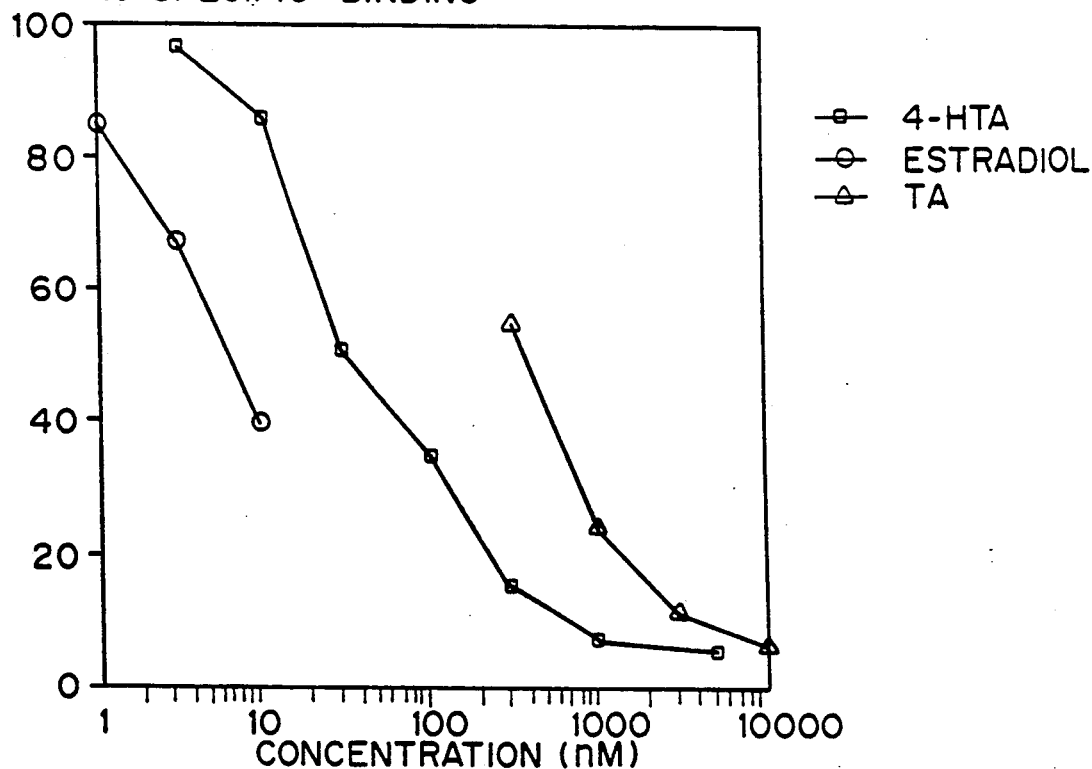
FIG. 2 is a graph of the effect of increasing concentrations (nM) of 4-HTA (—□—), estradiol (—O—), and TA (—◇—) on the binding of [$^3$H]estradiol in uterine cytosol from immature rats. Specifically bound $^3$H from [$^3$H]estradiol is plotted as a percentage of that bound in control incubations in the absence of 4-HTA, estradiol, or TA.

The estrogen receptor affinity of 4-hydroxy tamoxifen acid was measured according to the assay described in Example 2. FIG. 2 is a graph of the effect of increasing concentrations (nM) of 4-HTA (—□—), estradiol (—O—), and TA (—◇—) on the binding of [$^3$H]estradiol in uterine cytosol from immature rats. Specifically bound $^3$H from [$^3$H]estradiol is plotted as a percentage of that bound in control incubations in the absence of 4-HTA, estradiol, or TA. Estradiol and tamoxifen, the non-hydroxylated analog of 4-HTA, were used as standards. This data indicates that 4-HTA has an estrogen receptor affinity of 21% that of estradiol. Thus, 4-HTA is an excellent ligand for the estrogen receptor and this finding underscores the contribution of the hydroxyl group in 4-HTA to affinity. Tamoxifen acid also binds to the estrogen receptor.

EXAMPLE 4

Effect of Compounds of Formula I on the Growth of MCF7 Breast Cancer Cells

Breast cancer cells require estrogen or an estrogen substitute to grow. Antiestrogens inhibit the growth of breast cancer cells. The antiestrogenic effect of the nonsteroidal triarylethylene compounds of Formula I is measured by comparing the growth of MCF7 breast cancer cells in the presence and absence of the compounds, according to the method described below for 4-hydroxy tamoxifen acid.

Figure 3:
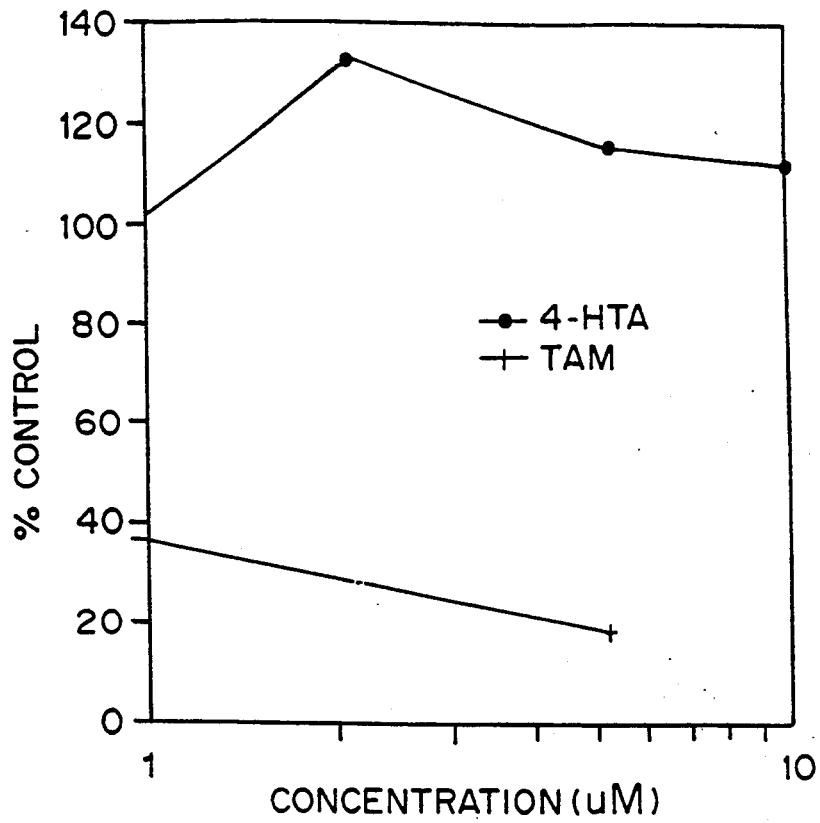
FIG. 3 is a graph of the effect of various concentrations ($\mu$M) of 4-HTA (—■—) and TAM (—+—) on MCF 7 human breast cancer cell proliferation.

4-HTA had no effect on proliferation of MCF 7 human breast cancer cells grown in the presence of estrogens, as shown in FIG. 3. Cells ($1 \times 10^5$) in exponential growth phase were plated into 25 cm$^2$ tissue culture flasks in 5 mL of RPMI 1640 culture medium supplemented with 10% fetal calf serum and other additives. When cell numbers had reached $2-2.5 \times 10^5$ per flask (approximately 72 h later), culture medium was changed and varying concentrations of drug were added as solutions in 5 uL aliquots of DMSO. Cell numbers were determined five days later, after approximately four population doublings in drug free controls. Data shown are expressed as percentages of cell numbers in control flasks and are averages of six estimates from two separate experiments. TAM, a known antiestrogen, was a potent inhibitor of cell growth. In contrast, 4-HTA does not possess anti-estrogenic activity.

EXAMPLE 5

Reversal of Antiestrogenic activity of TAM by 4-Hydroxy Tamoxifen Acid.

Figure 4:
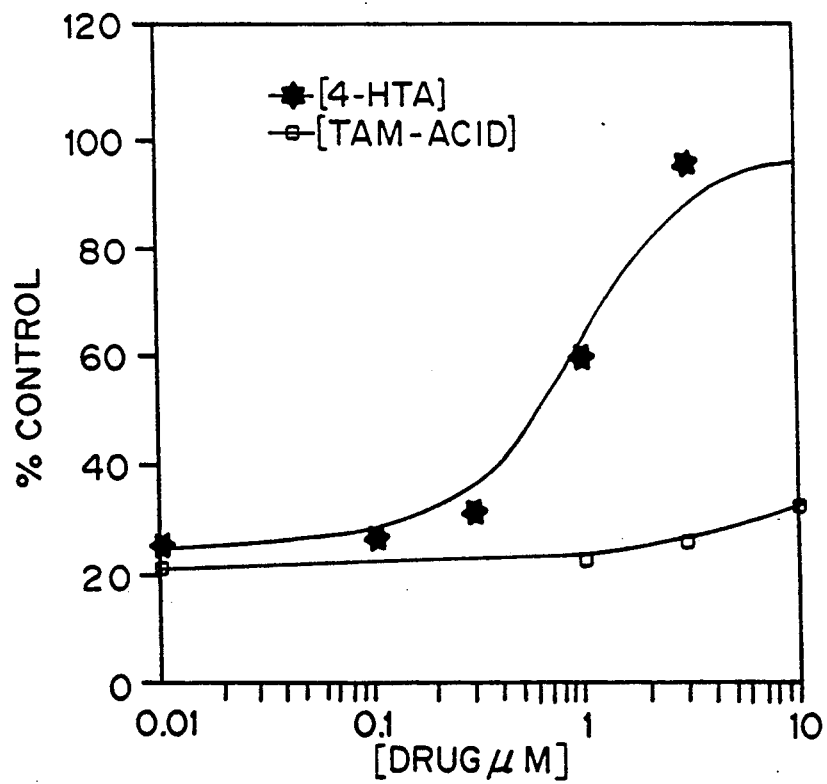
FIG. 4 is a graph illustrating the ability of 4-HTA (—*—) and TA (—□—) to reverse the effect of tamoxifen on MCF 7 cell growth, at various concentrations (μM).

As shown in FIG. 4, the inhibitory effect of 1 μM tamoxifen on MCF7 breast cancer cells was reversed in a dose dependent manner by 4-HTA, and, to a lesser extent, by TA. Cells were grown as summarized in Example 4 and tamoxifen was added to flasks as a solution in DMSO (5 mL), as were increasing concentrations of TA or 4-HTA. Data shown in FIG. 4 are expressed as percentages of cell numbers in drug free flasks and are averages of six estimates from two separate experiments. These findings demonstrate that 4-hydroxy tamoxifen acid does not possess antiestrogenic activity but instead can actually reverse the antiestrogenic effect of TAM.

This assay can also be used to measure the ability of other compounds in Formula I to reverse the antiestrogenic effect of TAM.

EXAMPLE 6

Stimulation of Estrogen Dependent Cell Proliferation

The ability of the triarylethylene carboxylic acids of Formula I to stimulate MCF 7 cell proliferation in cells grown in an estrogen free medium is demonstrated using estradiol as a standard for comparison. Cells were conditioned as described in Example 2, and then withdrawn from estrogen stimulation and incubated with phenol red free medium prepared with charcoal-stripped fetal calf serum. After five days, medium was changed and 4-HTA or estradiol were added as described in Example 2. After nine days, cell numbers were determined.

Figure 5:
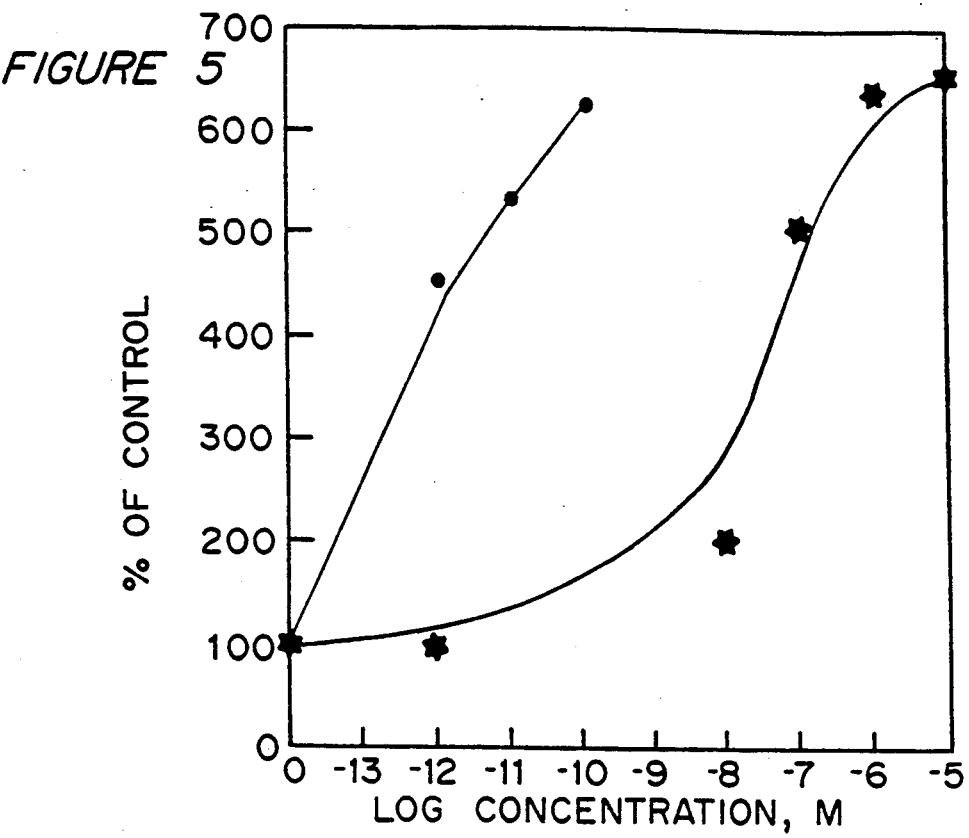
FIG. 5 is a graph illustrating the stimulatory effect of estradiol (—■—) and 4-HTA (—*—) at various concentrations (log concentration, μM) on MCF 7 cell growth.

As shown in FIG. 5, dose dependent stimulation of growth was seen with 4-HTA at submicromolar concentrations. Data shown are expressed as percentages of cell numbers in drug free flasks. Each point is the average of 3–6 determinations. Though not as potent as estradiol, 4-HTA stimulated growth to the same level as did estradiol, and this level did not decrease with further increases in 4-HTA concentration. These findings indicate that 4-HTA is a pure estrogen with no residual estrogen antagonist activity.

III. In Vivo Conversion of Tamoxifen to TA and 4-HTA Materials and Methods

E,Z- [$^{14}$C]TAM (specific activity: 21.6 mCi/mmol) was obtained from Amersham Corp., Arlington Heights, Ill. The radiolabel was uniformly distributed in the phenyl ring geminal to the one bearing the side chain. Preparative TLC ($20 \times 20$ cm silica gel GF$_{254}$, mm thickness—Analtech, Newark, Del.) using benzene/triethylamine (90.10, v/v) as developing solvent and unlabelled Z- and E,Z-TAM as external standards, afforded the pure Z-isomer. 4-HT was obtained from Dr. A.H. Todd of ICI Pharmaceuticals, Macclesfield, England. TAM bis-phenol and TA were prepared according to methods known in the art. 4-HTA was prepared according to the method set forth above in Example 1.

4-HTA appeared as a single spot by TLC using solvents 1-3 (below), and had the following spectral features: $^1$H NMR (CDCl$_3$) 0.90 (t, J=7 Hz, 3 H, CH$_2$CH$_3$), 2.45 (d, J=7 Hz, 2 H, CH$_2$CH$_3$), 4.50 and 4.66 (s, 1 H each, OCH$_2$C=O), 6.50-7.25 (m, 13 H, ArH); EIMS (direct ion probe, 70 eV) m/z 374 (100, M·+), 359 (20, M— Me), 315 (7, M—CH$_2$COOH). Coupling of TA with glycine ethyl ester using carbonyldiimidazole, according to methods known in the art, followed by saponification of the resulting amido ester, gave TA glyOH. This product had a TLC Rf of 0.34 (Solvent 2): $^1$H NMR (CD$_3$OD) 4.16 (s, 2 H, N—CH$_2$-C=O).

Chromatography. TLC was performed using plastic backed sheets (5×20 cm) coated with 0.2 mm silica gel GF$_{254}$ (Universal Scientific, Atlanta, Ga.). Plates were developed with chloroform/methanol/acetic acid mixtures (v/v) of the following compositions: (90:10:0.0, solvent 1; 90:10:0.5, solvent 2; 75:25:0.5, solvent 3).

Animals and Dosing. Female Sprague-Dawley rats, 45-55 grams each, were maintained on a normal laboratory diet and were divided into groups of four to six per experiment. Each animal received 28 mg (75 nmols, 1.62 mCi) of [$^{14}$C]TAM intraperitoneally in a volume of 0.2 ml. This solution was prepared by dissolving the drug in 10 ml of 1% citric acid in N,N-dimethylacetamide and diluting the solution with 0.2 ml of 1.15% aqueous KCl just before use. Animals were housed in polycarbonate metabolism cages equipped for separate collection of urine and feces.

Processing of Biological Samples. At 24 and 48 hours after dosing, animals were killed by decapitation. Uteri and livers were removed and weights were recorded. Pooled uteri, and livers were homogenized in 10 volumes of methanol. Each homogenate was centrifuged at 400×g for 10 min. Triplicate 1.0 ml aliquots of supernatants were counted for radioactivity in 8 ml of Ecoscint (National Diagnostics, Somerville, N.J.). Collected urine was lyophilized. The residue was sonicated in methanol, and the mixture was filtered and the solid residue was washed with methanol to make the final volume equal to the original urine volume. This procedure removed endogenous polar materials with no loss of radioactivity. Feces collected 24 and 48 hr after dosing were homogenized in 10 volumes of methanol. The homogenate was centrifuged and analyzed for radioactivity as described above.

Extraction and Analysis. Unlabelled TA and 4-HTA (10-20 g each) were added as standards to methanol extracts of tissues, urine, and feces. A third standard, TA glyOH, was added only to the urine extract. Each solution was then concentrated under a stream of N$_2$. To each residue was added 0.5 ml of 1% aqueous NaOH. The resulting mixture (pH≧11) was extracted serially two times with 1.0 ml portions of ether. Radioactivity present in these extracts was determined. To the aqueous phase was added 0.1 ml of 10% HCl, and the mixture (pH≦1) was extracted as before. Radioactivity was determined in some of these extracts. Otherwise, they were concentrated under a stream of N$_2$. Each residue was dissolved in 50 ml of acetone and the solution was applied to a TLC plate. Developed plates were segmented using the locations of reference compounds under UV light of 254 nm wavelength for guidance. Radioactivity was determined in segments containing reference compounds, and in some cases in all segments from TLC plates.

The specific activity of TA and 4-HTA eluted from developed chromatograms was determined by immersion of the segments containing these metabolites in a solution of 2.8% ammonia in methanol for 12 hr. Radioactivity in aliquots of eluates was determined, and quantities of TA and 4-HTA were estimated from absorbance of solutions at 283 nm using $e_{283} = 1.2 \times 10^4$ $M^{-1}cm^{-1}$ for each compound. Subsequent processing of eluates was conducted according to methods known in the art.

Effect of Deconjugating Enzymes on Recovery of Urinary Metabolites. An amount of methanolic urine extract, containing approximately 300,000 dpm, was concentrated. The residue was dissolved in 1.2 ml of 0.1M phosphate buffer, pH 7.4, and the solution was divided into three equal portions. To the first of these was added 100 units of β-glucuronidase; to the second, 20 units of β-glucosidase and 12 units of aryl sulfatase were added. These enzymes were obtained from Sigma Chemical Co., St. Louis, Mo. No enzymes were added to the third portion. After 18 hr at 25° C., each of the three aliquots was extracted and analyzed as described above.

Rat Liver Microsomal Glucuronidation of TAM Metabolites. An enzyme linked assay for UDP glucuronyl transferase in detergent-activated microsomes was used; enzyme linked assays such as this are known in the art. Substrates were added to incubation mixtures as solutions in 10 ml of N,N-dimethylacetamide. Each incubation (1.0 ml) contained UDP glucuronic acid (1.5 mM), substrate (10, 20, 50 or 100 mM), and Triton X-100 (80 mg). Incubations were started by addition of microsomal suspension containing 0.25 mg of protein (protein was determined according to standard methods known in the art) and were run under nitrogen at 37° C. for 30 min.

Identification of Acidic TAM Metabolites in Rats

Figure 6:
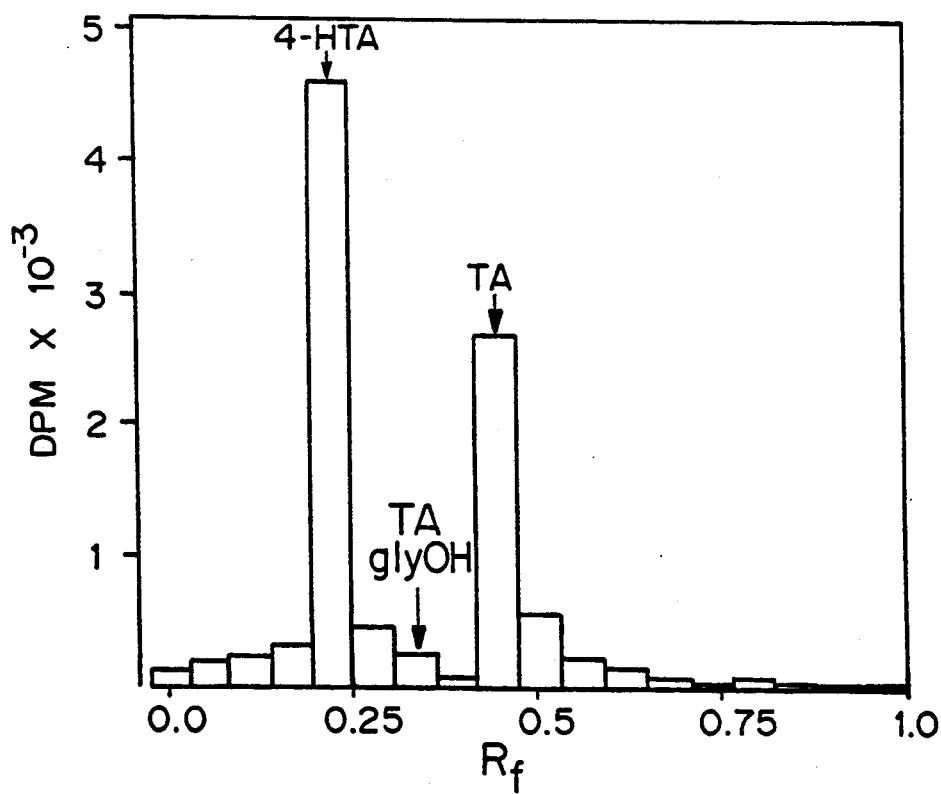
FIG. 6 is a radiochromatographic analysis of acidic urinary radioactivity ($R_f$ vs. DPM × $10^3$) on administration to rats of $^{14}C$ tamoxifen. Arrows indicate the locations of reference compounds, 4-HTA (4-hydroxy tamoxifen acid), TA glyOH ((Z)-N-4-(1,2-diphenyl-i-butenyl)phenoxyacetylglycine), and TA (tamoxifen acid), in the chromatogram.

Rats were treated with radioactively labeled TAM as described above and their urine was collected. FIG. 6 is a radiochromatographic analysis of acidic urinary radioactivity (R$_f$ vs. DPM×10$^{-3}$) on administration to rats of $^{14}$C tamoxifen. Arrows indicate the locations of reference compounds, 4-HTA (4-hydroxy tamoxifen acid), TA glyOH ((Z)-N-4-(1,2-diphenyl-1-butenyl)phenoxyacetylglycine), and TA (tamoxifen acid), in the chromatogram. This radioactivity was retained in the TA and 4-HTA fractions after three successive TLC purifications (Table 1), demonstrating that the radioactivity was incorporated into these compounds and establishing that TA and 4-HTA are final products of TAM metabolism.

TABLE 1

| Specific activity of urinary 4-HTA and TA after repetitive TLC analysis. | | |
|---|---|---|
| Compound | TLC Solvent | R$_f$ Specific Activity, nCi/mmol |
| TA | 1 | 0.39 8.2 |
| | 2 | 0.42 11.1 |
| | 3 | 0.33 8.3 |
| 4-HTA | 1 | 0.25 5.3 |
| | 2 | 0.31 5.0 |
| | 3 | 0.22 5.1 |

Localization of TAM Derived Radioactivity

While a significant amount of TAM-associated acidic radioactivity was eliminated in urine, only negligible levels of acidic radioactivity were detected in uterine tissue 24 hr after administration of [$^{14}$C]TAM (Table 2). This was also the case at 8 and 16 hr after administration. Modest levels of TA and 4-HTA were found in liver, and higher levels were found in fecal extracts. These results indicate that TAM is eliminated to a significant extent as acidic metabolites, namely TA and 4-HTA, in urine. This is in contrast to other, non-acidic, TAM metabolites which were found in these tissues under similar experimental conditions, as reported by Ruenitz, et al., "Comparative Fates of Clomiphene and Tamoxifen in the Immature Female Rat." *Drug Metab. Dispos.* 13:582–586 (1985).

TABLE 2

Distribution and elimination of TA and 4-HTA after intraperitoneal administration of [$^{14}$C]TAM[a].

| Specimen | Time After Dosing, hr | Percent of Dose Present as: | | |
|---|---|---|---|---|
| | | Total $^{14}$C | TA | 4-HTA |
| feces | 0–24 | 30.49 | 0.50 | 2.40 |
| feces | 24–48 | 16.05 | 0.46 | 1.43 |
| urine | 0–24 | 8.70 | 1.02 | 1.81 |
| liver | 24 | 20.25 | 0.06 | 0.41 |
| liver | 48 | 2.84 | b | b |
| uterus | 24 | 0.12 | b | b |

[a]Values are ±5% on determinations from aliquots.
[b]Radioactivity present in extracts prior to chromatography did not differ from background.

Carboxylic acids are often subject to further metabolic alteration via amino acid and/or carbohydrate conjugation. In the rat, this can involve glycine, and occasionally, taurine and glucuronic acid. Treatment of urine extract with either β-glucuronidase or β-glucosidase/aryl sulfatase, that cleave these conjugates, resulted in no change in the amount of ether-extractable acidic radioactivity. In contrast, the amount of radioactivity in the basic/neutral fraction was increased 55% by the first deconjugating enzyme. These results were consistent with in vitro studies of the interaction of TAM metabolites with UDP glucuronyl transferase (Table 3). Thus, while TAM bis-phenol and 4-HT were substrates for these enzymes, 4-HTA was not a substrate under these conditions, indicating that neither TA nor 4-HTA is subject to urinary elimination as these conjugates. In contrast, the methyl ester of 4-HTA was an excellent substrate for the enzyme, indicating that the strong acidity of 4-HTA, or insufficient lipid solubility, an important property of substrates, may obviate interaction with the enzyme.

TABLE 3

Rat liver microsomal glucuronidation of selected compounds.

| Substrate | $K_m$, mM | $V_{max}$, nmols/mg-min |
|---|---|---|
| 4-HT | 83 | 7.4 |
| 4-HTA | — | 0.0[a] |
| Methyl 4-HTA | 73 | 16.5 |
| TAM bis-phenol | 54 | 14.7 |
| TA | — | 0.0[a] |
| p-Bromophenol | 312 | 15.6 |

Each result is the average of two to three experiments.
[a]No activity was observed at substrate concentrations of 100 mM.

Together, these findings demonstrate that in the immature female rat 4-HTA is eliminated unchanged in the urine. This is in contrast to estradiol and other estrogens bearing hydroxyl substituents, the presence of which generally exposes these high potency estrogens to rapid elimination via metabolic conjugation. These findings further indicate that TAM acid analogues have a relatively long retention time in the body and suggest a potential for prolonged action of this structural type. Also, in stark contrast to estradiol, 4-HTA was not detected in uterine or ovarian tissue in this animal species. Thus, estrogenic effects of this structural type must be due to interaction with estrogen receptors other than those found in these organs.

III. Pharmaceutical Compositions

The nonsteroidal estrogenic triarylethylene carboxylic acids of Formula I can be administered topically, subcutaneously, intravenously, orally, intraperitoneally or via implantable extended release devices. The active compounds can be administered as the free acid or as a pharmaceutically acceptable salt, including the sodium, potassium, or tromethamine salt. The compounds can be combined with acceptable pharmaceutical carriers or diluents. Pharmaceutically acceptable carriers and methods for the compounds with such carriers are known and will be obvious to one skilled in the art. The active compound may be enclosed within gelatin capsules, compressed into tablets, suspended or dissolved in solution, incorporated into controlled release devices, or incorporated into liposomes. For the purposes of oral therapeutic administration, the active compound can be combined with excipients and pharmaceutically compatible binding agents, and/or adjuvant materials can be included as part of the composition.

Tablets, pills, capsules, troches and the like may contain any of the following ingredients, or compounds of a similar nature: a binder such as microcrystalline cellulose, gum tragacanth or gelatin; an excipient such as starch or lactose, a disintegrating agent such as alginic acid, Priomgel, or corn starch; a lubricant such,as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, syrup, elixir, or suspension it can contain, in addition to material of the above type, a liquid carrier such as a fatty oil. When the dosage unit form is a suspension, solution, or topical composition it may contain sterile diluent such as water, saline solution, polyethylene glycols, glycerine, propylene glycol, and/or various buffers such as phosphate, acetate, and citrate. The compounds can be combined with pharmaceutical creams or ointments. If administered intravenously, preferred carriers are physiological saline or phosphate buffered saline (PBS).

The active compounds can also be incorporated into controlled release compositions. Biodegradable, biocompatible polymers, such as polyanhydrides, ethylene vinyl acetate, polyglycolic acid, can be used to control the rate of release of the active ingredient in the body.

The triarylethylene carboxylic acids can be incorporated into liposomes. Liposomes may be prepared according to methods known to those skilled in the art, for example, as described in U.S. Pat. No. 4,522,811 (which is incorporated herein by reference in its entirety).

The active compounds can be further mixed with other active materials that do not impair the estrogenic activity of the active compounds, including antibiotics, antifungals, antivirals, and anti-inflammatories.

The triarylethylene carboxylic acids are administered in any effective amount to alleviate a medical condition treatable with estrogen. Preferably, the compounds are administered in the range of 10 mg/day to 1000 mg/day, and more preferably between 20 and 40 mg/day, or 0.15 to 15 mg/kg of body weight per day, and preferably between 0.29 and 0.58 mg/kg of body weight per day. The effective dosage and mode of administration will vary depending on the patient to be treated, the condition to be treated, and the severity of the condition to be treated. The effective dosage and mode of administration suitable for a particular patient having a particular medical need is ascertainable by one skilled in the art.

Modifications and variations of the present invention, tamoxifen acid analogues possessing estrogenic activity and methods of synthesis and use thereof, will be obvious to one skilled in the art from the foregoing detailed description of the invention. Such modifications and variations are intended to come within the scope of the appended claims.

I claim:

1. A triarylethylene carboxylic acid of the structure:

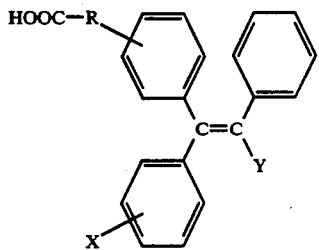

wherein R is $(CH_2)_mO$ or $(CH_2)_n$, m is 1, 2, 3, or 4, and n is 0, 1, 2, 3, or 4; X is hydrogen or hydroxyl, Y is methyl, ethyl, chlorine, or bromine, wherein the RCOOH an X moieties are either metal or para to the phenyl ethylene linkage, and wherein when X is hydrogen, R is not $(CH_2)_nO$.

2. The compound of claim 1 wherin Y is selected from the group consisting of ethyl and chloro.

3. The compound of claim 1 wherein X is hydroxyl.

4. The compound of claim 1 wherein R is $CH_2O$.

5. The compound of claim 1 in the Z configuration.

6. The compound of claim 1 that is a mixture of Z and E isomers.

7. The compound of claim 1 in the E configuration.

8. The compound of claim 1 wherein X is in the para position.

9. The compound of claim 1 that is 4-hydroxy tamoxifen acid.

10. The compound of claim 1 selected from the group consisting of 3-HTA, 4-[1-(p-hydroxyphenyl)-2-phenyl-1-butenyl]benzoic acid and 4-[1-(p-hydroxyphenyl)-2-phenyl-1-butenyl]phenylacetic acid.

11. A pharmaceutical composition comprising an effective amount of a triarylethylene carboxylic acid of the formula

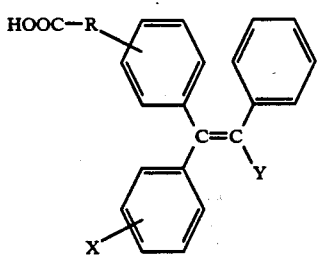

wherein R is $(CH_2)_mO$ or $(CH_2)_n$, m is 1, 2, 3, or 4, and n is 0, 1, 2, 3, or 4; X is hydrogen or hydroxyl, Y is methyl, ethyl, chlorine, or bromine; wherein the RCOOH and X moieties are either meta or para to the phenyl ethylene linkage, and wherein when X is H, R is not $(CH_2)_nO$; or its pharmaceutically acceptable salt, in a pharmaceutically acceptable carrier.

12. The pharmaceutical composition of claim 11 comprising a pharmaceutically acceptable carrier selected from the group consisting of topical carriers, subcutaneously injectable carriers, intravenously injectable carriers, orally ingestible carriers, and implantable extended release biocompatible and biodegradable carriers.

13. The pharmaceutical composition of claim 11 that includes between approximately 10 and 1000 mg of the triarylethylene carboxylic acid.

14. The pharmaceutical composition of claim 11 that includes between approximately 20 and 40 mg of the triarylethylene carboxylic acid.

15. A method to alleviate a condition treatable with estrogen comprising:
administering to a mammalian patient an effective amount of a compound having the structure of

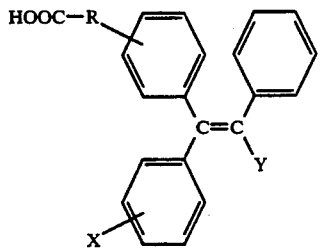

wherein R is $(CH_2)_mO$ or $(CH_2)_n$, m is 1, 2, 3, or 4, and n is 0, 1, 2, 3, or 4; X is hydrogen or hydroxyl, Y is methyl, ethyl, chlorine, or bromine; wherein the RCOOH and X moieties are either meta or para to the phenyl ethylene linkage, or its pharmaceutically acceptable salt, in a pharmaceutically acceptable carrier.

16. The method of claim 15 wherein Y is selected from the group consisting of ethyl and chloro.

17. The method of claim 15 wherein X is hydroxyl.

18. The method of claim 15 wherein R is $CH_2O$.

19. The method of claim 15 wherein the triarylethylene carboxylic acid is in the Z configuration.

20. The method of claim 15 wherein the triarylethylene carboxylic acid is a mixture of Z and E isomers.

21. The method of claim 15 wherein the triarylethylene carboxylic acid is in the E configuration.

22. The method of claim 15 wherein X is in the para position.

23. The method of claim 15 wherein the triarylethylene carboxylic acid is selected from the group consisting of 4-hydroxy tamoxifen acid and tamoxifen acid.

24. The method of claim 15 wherein the triarylethylene carboxylic acid is selected from the group consisting of 3-HTA, -[1-(p-hydroxyphenyl)-2-phenyl-1-butenyl]benzoic acid and 4-[1-p-hydroxyphenyl)-2-phenyl-1-butenyl]phenylacetic acid.

25. The method of claim 15 wherein the pharmaceutically acceptable carrier is selected from the group consisting of topical carriers, subcutaneously injectable carriers, intravenously injectable carriers, orally ingestible carriers and implantable extended release biocompatible and biodegradable carriers.

26. The method of claim 15 wherein the amount of triarylethylene carboxylic acid administered is in the range of 10 mg/day to 1000 mg/day.

27. The method of claim 15 wherein the amount of triarylethylene carboxylic acid administered is in the range of 20 mg/day to 40 mg/day.

28. The method of claim 15 wherein the amount of triarylethylene carboxylic acid administered is in the range of 0.15 to 15 mg/kg of body weight per day.

29. The method of claim 15 wherein the amount of triarylethylene carboxylic acid administered is in the range of 0.29 to 0.58 mg/kg of body weight per day.

* * * * *

UNITED STATES PATENT AND TRADEMARK OFFICE
CERTIFICATE OF CORRECTION

PATENT NO. : 5,189,212

DATED : February 23, 1993

INVENTOR(S) : Peter C. Reunitz

It is certified that error appears in the above-identified patent and that said Letters Patent is hereby corrected as shown below:

```
Column 4, line 38, please replace the first "(" in
"(1,2-diphenyl-1-[4-(2-dimethyl-" with a "{".
Column 5, line 27, please delete "of4-(2-bromoethoxy)-4'-
hvdroxybenzophe-" and insert --of 4-(2-bromoethoxy)-4'-
hydroxybenzophe--- in place thereof.
Column 5, line 51, please delete "(E,Z)-2-(4-[1-(4-
hydroxyphenyl)-" and insert --(E,Z)-2-{4-[1-(4-
hydroxyphenyl)-- in place thereof.
Column 5, line 59, please delete "th" and insert --the- in
place thereof.
Column 7, line 2, please delete the second "µ" in
"200-µµL".
Column 7, line 8, please delete "nonspeoifio" and
insert --non-specific-- in place thereof.
Column 7, line 14, delete "buffer]is" and insert
--buffer] is-- in place thereof.
```

UNITED STATES PATENT AND TRADEMARK OFFICE
CERTIFICATE OF CORRECTION

PATENT NO. : 5,189,212

DATED : February 23, 1993

INVENTOR(S) : Peter C. Reunitz

Page 2 of 2

It is certified that error appears in the above-identified patent and that said Letters Patent is hereby corrected as shown below:

Column 12, line 27, please delete "Priomgel" and insert --Primogel-- in place thereof.
Column 12, line 27, delete "such,as" and insert --such as-- in place thereof.
Column 12, line 46, please insert --and-- before "polyglycolic acid".

Signed and Sealed this

Twenty-fourth Day of October, 1995

Attest:

BRUCE LEHMAN

*Attesting Officer*  Commissioner of Patents and Trademarks